(12) United States Patent
Diehl et al.

(10) Patent No.: US 7,709,644 B2
(45) Date of Patent: May 4, 2010

(54) PROCESS FOR THE ENANTIOMERIC ENRICHMENT OF CIS-8-BENZYL-7,9-DIOXO-2,8-DIAZABICYCLO[4.3.0]NONANE

(75) Inventors: Herbert Diehl, Leverkusen (DE); Andreas Krebs, Odenthal (DE); Elvira Krebs, legal representative, Odenthal (DE); Walter Lange, Odenthal (DE); Hanns-Ingolf Paul, Leverkusen (DE); Dietrich Seidel, Wuppertal (DE); Rolf Grosser, Leverkusen (DE); Tobias Reichelt, Köln (DE)

(73) Assignee: LANXESS Deutschland GmbH, Leverkusen (DE)

( * ) Notice: Subject to any disclaimer, the term of this patent is extended or adjusted under 35 U.S.C. 154(b) by 200 days.

(21) Appl. No.: 11/651,309

(22) Filed: Jan. 9, 2007

(65) Prior Publication Data

US 2007/0213536 A1    Sep. 13, 2007

Related U.S. Application Data

(63) Continuation of application No. 10/463,597, filed on Jun. 17, 2003, now abandoned.

(30) Foreign Application Priority Data

Jun. 17, 2002    (DE) ................... 10226923

(51) Int. Cl.
    C07D 487/04    (2006.01)
(52) U.S. Cl. ................... 546/113
(58) Field of Classification Search ........... 546/113
    See application file for complete search history.

(56) References Cited

U.S. PATENT DOCUMENTS

| | | | |
|---|---|---|---|
| 2,621,149 A | 12/1952 | Scott et al. | 196/147 |
| 2,985,589 A | 5/1961 | Broughton et al. | 210/34 |
| 4,942,149 A | 7/1990 | Shinbo et al. | 502/401 |
| 4,990,517 A | 2/1991 | Petersen et al. | 514/300 |
| 5,059,597 A | 10/1991 | Petersen et al. | 514/224.5 |
| 5,287,222 A | 2/1994 | Uozu et al. | 359/654 |
| 5,416,096 A | 5/1995 | Petersen et al. | 514/312 |
| 5,496,937 A | 3/1996 | Okamoto et al. | 536/124 |
| 5,607,942 A | 3/1997 | Petersen et al. | 546/200 |
| 6,217,769 B1 | 4/2001 | Okamoto et al. | 210/635 |
| 6,277,782 B1 | 8/2001 | Moller et al. | 502/402 |
| 6,333,426 B1 | 12/2001 | Moller et al. | 560/25 |
| 6,372,127 B1 * | 4/2002 | Ikeda | 210/93 |

FOREIGN PATENT DOCUMENTS

| | | |
|---|---|---|
| EP | 550 903 | 12/1992 |
| EP | 1 118 623 | 7/2001 |
| WO | 92/16274 | 10/1992 |
| WO | 0076996 | 12/2000 |

OTHER PUBLICATIONS

Juza et al., "Simulated moving-bed, etc.," Tibtech, Mar. 2000, 18, 108-118.*
Blehaut et al., "Recent aspects, etc.," Analusis Magazine, 1998, 26(7), 60-M70.*
M. Negawa and F. Shoji, Journal of Chromatography, 590, (month unavailable) 1992, pp. 113-117, Elsevier Science Publishers B.V., Amsterdam, "Optical resolution by simulated moving-bed adsorption technology".
Schulte M et al: "Preparative enantioseparation by a simulated moving bed chromatography" Journal of Chromatography, Elsevier Science Publishers B.V. Amsterdam, NL, Bd. 906, Nr. 1-2 Jan. 12, 2001, Setien 399-416, XP004227671 ISSN: 0021-9673 * Seite 402, Spalte 1, Absatz 2 * * Seite 403; Abbildunq * *Seite 411; Tablle 6*.

* cited by examiner

*Primary Examiner*—Patricia L Morris
(74) *Attorney, Agent, or Firm*—Michael A. Miller

(57) ABSTRACT

The present invention relates to a process for the enantiomeric enrichment of cis-8-benzyl-7,9-dioxo-2,8-diazabicyclo [4.3.0]nonane with the aid of continuous countercurrent chromatography, which is also described as SMB chromatography (SMB=simulated moving bed).

In a further aspect, the invention relates to a process for the preparation of (1S,6R)-8-benzyl-7,9-dioxo-2,8-diazabicyclo [4.3.0]nonane using the aforementioned process, which furthermore includes a racemization step.

23 Claims, No Drawings

PROCESS FOR THE ENANTIOMERIC ENRICHMENT OF CIS-8-BENZYL-7,9-DIOXO-2,8-DIAZABICYCLO[4.3.0]NONANE

This application is a continuation of U.S. application Ser. No. 10/463,597, filed Jun. 17, 2003 now abandoned, entitled Process for the Enantiometric Enrichment of CIS-8-Benzyl-7,9-Dioxo-2,8-Diazabicyclo[4.3.0]Nonane, incorporated herein by reference, which claims priority to German Application No. 102 26 923.8, filed Jun. 17, 2002.

BACKGROUND OF THE INVENTION

1. Field of the Invention

The present invention relates to a process for the enantiomeric enrichment of cis-8-benzyl-7,9-dioxo-2,8-diazabicyclo-[4.3.0]nonane with the aid of continuous countercurrent chromatography, in particular, SMB chromatography (SMB=simulated moving bed). In a further aspect, the invention relates to a process for the preparation of (1S,6R)-8-benzyl-7,9-dioxo-2,8-diazabicyclo[4.3.0]nonane using the aforementioned process, which furthermore includes a racemization step.

2. Brief Description of the Prior Art

The enantiomers of cis-8-benzyl-7,9-dioxo-2,8-diazabicyclo[4.3.0]nonane (DOPP) are valuable intermediates for the preparation of quinolone- and naphthyridone-carboxylic acid derivatives which, inter alia, have gained great industrial importance as an active constituent of antibacterial agents and food additives (EP-A 550 903).

(1S,6R)-8-Benzyl-7,9-dioxo-2,8-diazabicyclo[4.3.0]nonane of the formula (Ia)

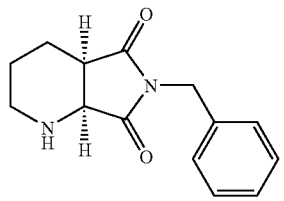

(Ia)

is, for example, a valuable intermediate for the preparation of (S,S)-2,8-diazabicyclo[4.3.0]nonane (IIa),

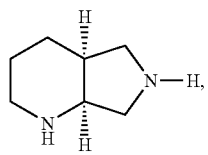

(IIa)

into which it can be converted by reduction of the carbonyl groups and debenzylation in a manner known per se (EP-A 350 733). (S,S)-2,8-Diazabicyclo[4.3.0]nonane is, for its part, used for the preparation of the antibiotic moxifloxacin (INN, 1-cyclo-propyl-7-([S,S]-2,8-diazabicyclo[4.3.0]non-8-yl)-6-fluoro-1,4-dihydro-8-methoxy-4-oxo-3-quinolonecarboxylic acid, (III)) (EP-A 350 733): (III)

The enantiomer (1R,6S)-8-benzyl-7,9-dioxo-2,8-diazabicyclo[4.3.0]nonane (Ib)

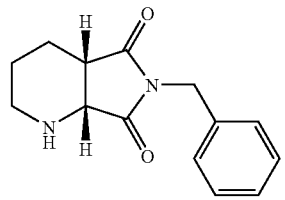

(Ib)

is in turn a valuable intermediate for the preparation of (R,R)-2,8-diazabicyclo[4.3.0]nonane (IIb),

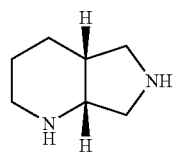

(IIb)

which can likewise be used for the preparation of very active antibacterial agents (e.g. Interscience Conference on Antimicrobial Agents and Chemotherapy (ICAAC), 1996, Abstr. No. F-001).

Processes for the enantiomeric enrichment of cis-8-benzyl-7,9-dioxo-2,8-diazabicyclo[4.3.0]nonane are known in principle.

Thus, for example, EP-A 550 903 discloses a process for the resolution of cis-8-benzyl-7,9-dioxo-2,8-diazabicyclo [4.3.0]nonane using tartaric acid (Example A, Method IV and Example B, Method II a)). The processes described there require, for the preparation of the (1S,6R)-enantiomer, repeated recrystallization of the diastereomeric D-(−)-tartaric acid salts or reaction with L-(+)-tartaric acid and subsequent reaction of the released mother liquor with D-(−)-tartaric acid and recrystallization. The enantiomeric excesses obtained are, at 93.8% ee for the (1R,6S) enantiomer and 96.6% ee for the (1S,6R) enantiomer, inadequate with respect to the large number of operations and the large amount of chiral auxiliary reagants and thus only of limited suitability for industrial use.

EP-A 1 192 153 discloses a process for the resolution of cis-8-benzyl-7,9-dioxo-2,8-diazabicyclo[4.3.0]nonane, which, inter alia, employs (−)-2,3:4,6-di-O-iso-propylidene-2-keto-L-gulonic acid and camphorsulphonic acid as chiral auxiliary reagents. However, here too, the amount of chiral auxiliary reagent needed and the large number of working steps restricts industrial use.

There was therefore the need for an efficient process for the enantiomeric enrichment of cis-8-benzyl-7,9-dioxo-2,8-diazabicyclo[4.3.0]nonane, in which the separated enantiomers can be prepared on an industrial scale and in high absolute and optical purity.

SUMMARY OF THE INVENTION

Surprisingly, a process for the enantiomeric enrichment of cis-8-benzyl-7,9-dioxo-2,8-diazabicyclo[4.3.0]nonane has now been found, which is characterized in that the enantiomeric enrichment is carried out by continuous countercurrent chromatography.

The term "enantiomeric enrichment" is to be understood in the context of the invention in that a starting mixture, which contains the two enantiomers of cis-8-benzyl-7,9-dioxo-2,8-diazabicyclo[4.3.0]nonane, (1S,6R)- and (1R,6S)-8-benzyl-7,9-dioxo-2,8-diazabicyclo[4.3.0]nonane, is separated in such a manner that after the separation the enantiomers are present in higher optical purity than before the separation.

It may be pointed out that in the context of the invention, the definitions, parameters and explanations, which are general or mentioned in preferred ranges, can be combined with one another in any desired manner, i.e. also between the respective ranges and preferred ranges, and these combinations are also included in the scope of the invention.

DETAILED DESCRIPTION OF THE INVENTION

For the process according to the invention, there is preferably employed a starting mixture which contains the enantiomers in a molar ratio of 0.25:1 to 4:1 and preferably 0.8:1 to 1.25:1. Particularly preferably, the starting mixture contains the racemic mixture of the enantiomers.

The optical purity is indicated below by the "enantiomeric excess" (ee), which is defined as:

$$ee\ [S]=(m[S]-m[R])/m(S+R)$$

where ee(S) is the optical purity of the enantiomer S, m(S) is the amount of substance of the enantiomer S and m(R) is the amount of substance of the enantiomer R. It is customarily given in percent enantiomeric excess (% ee=ee/100).

cis-8-Benzyl-7,9-dioxo-2,8-diazabicyclo[4.3.0]nonane can advantageously be obtained as a racemic mixture according to EP-A 350 733 by nuclear hydrogenation of pyridine-2,3-dicarboxylic acid N-benzylimide. In this preparation method, in principle the trans compounds diastereomeric to the cis compounds can also be obtained as by-products. Furthermore, other organic by-products can also be produced. It has surprisingly been found that the enantiomeric enrichment according to the invention can also be carried out in the presence of these by-products.

The invention therefore also comprises a process in which the enantiomeric enrichment of cis-8-benzyl-7,9-dioxo-2,8-diazabicyclo-[4.3.0]nonane is carried out in the presence of the enantiomeric trans-8-benzyl-7,9-dioxo-2,8-diazabicyclo-[4.3.0]nonanes and/or other organic by-products originating from the nuclear hydrogenation of pyridine-2,3-dicarboxylic acid N-benzylimide.

Their mass content, based on the starting mixture employed for the process according to the invention, which contains the enantiomers of cis-8-benzyl-7,9-dioxo-2,8-diaza-bicyclo[4.3.0]nonane, can be, for example, 0.01 to 20%, and customarily 0.5 to 10%.

The principle of continuous countercurrent chromatography for the separation of chiral compounds is known, for example, from M. Negawa and F. Shoji, J. Chrom. 590, 1992, pages 113-117. Suitable units for carrying out continuous countercurrent chromatography such as, in particular, SMB units are described, for example, in U.S. Pat. No. 2,621,149; U.S. Pat. No. 2,985,589 and WO 92/16274 and are commercially obtainable.

Here, in general a stream of liquid moving in one direction and optionally circulating is produced in an SMB unit by means of two or more segments connected to one another, each segment having at least one column filled with a chiral stationary phase and being provided in the flow direction at least with a liquid inlet and a liquid outlet and each segment having at least one inlet, via which a feedstream or an eluting agent can be fed to the optionally circulating stream of liquid, and furthermore having at least one outlet, via which solutions of the more weakly adsorbing compound (raffinate) or solutions of the more strongly adsorbing compound (extract) can be removed from the optionally circulating stream of liquid.

During operation of the SMB unit, the inlets and outlets are periodically, but not necessarily simultaneously, connected further in the direction of the flow of liquid, for example, via valves such as, for example, individual valves, multiway valves, valve blocks, flaps or rotation valves, such that apparently a countercurrent movement of the stream of liquid and stationary phase results. On account of this, the optionally circulating stream of liquid can be divided into four zones, in which the individual segments can have different functions.

In Zone I, which is situated between the inlet for the eluting agent and the outlet for the extract, the more strongly adsorbing compound is desorbed from the stationary phase.

In Zone II, which is situated between the outlet for the extract and the inlet for the feedstream, the more weakly adsorbing compound is desorbed from the stationary phase.

In Zone III, which is situated between the inlet for the feedstream and the outlet for the raffinate, the more strongly adsorbing compound is adsorbed from the stationary phase.

In Zone IV, which is situated between the outlet for the raffinate and the inlet for the eluting agent, the more weakly adsorbing compound is adsorbed from the stationary phase.

The zones can consist, for example, of one or more segments. The number of segments per zone can change here, however. In special cases, it can be advantageous that a zone consists during a period of a liquid compound, but not of segments or columns.

In certain cases, it can be advantageous to connect the individual segments of the abovementioned device one after the other, not in an endless sequence (closed circulation), but in a series of individual segments having an inlet at the beginning of the segment series and an outlet at the end of the segment series. In this case, an open circulation is referred to. Here, a part flow or the entire flow of the fluid, which is obtained via the outlet of the segment series, can be recirculated to the inlet of the segment series directly or after suitable treatment.

Advantageous treatment methods are, for example, intermediate storage, testing, distillation, removal of components by means of membrane processes, mixing, temperature-controlling and others.

In the context of the invention, the operation of an SMB unit as a closed circulation (with a circulating stream of liquid) is preferred.

In the context of the invention, it is advantageous to employ a column number from 4 to 24, preferably 5 to 12 and particularly preferably 5 to 8.

Preferably, the columns are designed as cylindrical axial flow columns, which have a device for the dynamic compression of the chiral stationary phase in the axial direction. However, columns of other structural designs can also be employed.

The column diameter, i.e. the diameter of the packing of the chiral phase, can be, for example, 5 to 1500 mm, preferably 50 to 1200 mm and particularly preferably 200 to 1200 mm. The column length, i.e. the length of the packing of the chiral phase in the flow direction, can be, for example, 15 mm to 300 mm, preferably 40 mm to 170 mm.

It has proved advantageous to use columns whose packing has a diameter-length ratio of 0.25 to 20, particularly preferably 1 to 5.

Suitable chiral stationary phases are in particular those which contain the derivatives of polysaccharides, chiral polyacrylates or chiral crown ethers and which are optionally and preferably applied to a support material.

Suitable chiral stationary phases are in particular those which contain derivatives of polysaccharides, optically active poly(acryl)amides, optically active network polymers or chiral crown ethers and which are optionally and preferably applied to a support material.

Such chiral stationary phases optionally applied to support materials are disclosed, for example, in EP-A 358 129, EP-A 1 118 623, EP-A 978 498, EP-A 625 524, EP-A 527 239 and EP-A 671 975.

Suitable support materials are, for example, inorganic or organic support materials which are preferably porous. For use in the process according to the invention, porous inorganic support materials are preferred.

Organic support materials are, for example, polymers such as polystyrenes, polyacrylic acid derivatives or their copolymers.

Inorganic support materials are, for example, silicon compounds such as silicas, silica gels and silicic acids, silicates such as zeolites, aluminium compounds such as aluminas, aluminium oxides, aluminates, titanium compounds such as titanium dioxides and titanates, magnesium compounds such as magnesia, riglasses, kaolin or apatites such as, in particular, hydroxyapatite. Some of the support materials mentioned can occur in various modifications, which are likewise included.

Silica gels are particularly preferred as support materials.

The particles of the support material advantageously have an average diameter (based on the particle count) of 0.1 μm to 1 mm, preferably 1 μm to 500 μm.

Furthermore, the particles of the support material advantageously have an average pore size of 10 Å to 50 μm.

Preferred polyacrylates are those which contain structural units of the formula (IV)

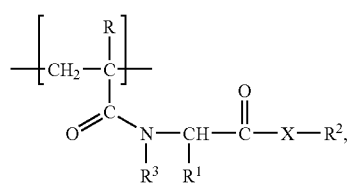

(IV)

where in formula (IV)
R represents hydrogen or methyl,
$R^1$ represents an alkyl group having 1 to 18 C atoms or a cycloalkyl group having 3 to 8 C atoms, each of which is optionally substituted by hydroxyl, halogen, alkoxy or cycloalkyl having up to 8 carbon atoms, by an aryl group having up to 14 carbon atoms or by a heteroalkyl having 4 to 14 carbon atoms, which contains 1 or 2 heteroatoms from the group consisting of nitrogen, oxygen and sulphur, where the aryl or heteroaryl groups mentioned are optionally substituted by hydroxyl, halogen, alkyl or alkoxy in each case having 1 to 4 C atoms,
$R^3$ represents hydrogen or together with $R^1$ represents a tri- or tetramethyllene group,
X represents oxygen or an $NR_4$ group, in which $R^4$ together with $R^2$ and the nitrogen atom form a 5- to 7-membered heterocyclic ring, which is optionally substituted with a COO-alkyl group (1 to 4 C atoms) or by 1 or 2 alkyl groups (in each case 1 to 4 C atoms), and $R^2$ represents a bulky highly space-filling hydrocarbon radical having up to 30 carbon atoms or a heteroaryl radical having 4 to 14 carbon atoms, which contains 1 heteroatom from the group consisting of nitrogen, oxygen or sulphur, where the hydrocarbon and heteroaryl radicals mentioned are optionally substituted by halogen, hydroxyl, alkyl and/or alkoxy in each case having 1 to 8 carbon atoms, with the proviso that, if $R^2$ is a tertiary butyl group or X represents the radical $NR^4$, R must be a methyl group.

For $R^1$, optionally substituted alkyl, cycloalkyl, aralkyl, aryl and heteroaryl radicals which may preferably be mentioned are the following radicals:

optionally substituted alkyl radicals the methyl, ethyl, i-propyl, n-propyl, n-butyl, i-butyl, sec-butyl, tert-butyl, 1-hydroxyethyl, 2-alkoxycarbonyl, 3-alkoxycarbonyl, 3-N-acylaminopropyl, 4-N-acylaminobutyl or tert-butoxy-methyl radical and the hydroxymethyl radical;

optionally substituted cycloalkyl radicals the cyclohexyl radical and the tetrahydronaphth-2-yl radical;

optionally substituted aralkyl radicals the benzyl radical and 4-hydroxybenzyl radical;

optionally substituted aryl radicals the phenyl radical and naphthyl radical;

optionally substituted heteroaryl radical the indol-3-yl radical.

For $R^2$, highly space-filling radicals which may be mentioned are, for example:

tertiary alkyl radicals such as the tert-butyl radical, the neopentyl radical and the adamantyl radical;

alkyl radicals substituted in the 1-position by cycloalkyl groups, such as the cyclohexylmethyl radical or cyclohexylethyl radical or cyclopropylmethyl radical;

optionally substituted cycloalkyl radicals such as the cyclohexyl radical and the cyclohexyl radicals substituted by methyl groups or tert-butyl groups such as the 2- or 3-methylcyclohexyl radical, the 4-tert-butyl radical and 2,6-di-tert-butylcyclohexyl radical or the decahydronaphthyl radical;

aralkyl radicals such as the 1-phenylethyl radical and the 2-phenylpropyl radical;

optionally substituted phenyl radicals such as the phenyl radical or phenyl radicals substituted by $C_1$-$C_4$-alkyl groups such as the o-tolyl radical, 2,6-xylyl radical, 4-tert-butyl radical and 2,6-di-tert-butyl-phenyl radical;

terpenyl radicals such as the menthyl, neomenthyl, bornyl, fenchyl and pinanyl radical.

Particularly advantageous is the use of optically active radicals for $R^2$, e.g. of the d- or l-1-phenylethyl radical or of the d- or l-methyl, d- or l-neomenthyl, d- or l-bornyl, d- or l-fenchyl radical or of the d- or l-pinanyl radical.

The polyacrylamides which contain the structural elements of the formula (VI) are preferably obtainable by polymerization of optically active N-(meth)acryloylamino acid derivatives of the formula (V)

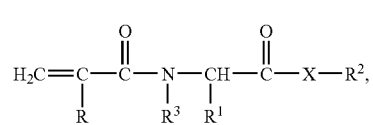

(V)

in which R, $R^1$, $R^2$ and $R^3$ have the meaning mentioned under the formula (IV). Particularly preferred polyacrylates and N-(meth)acryloylamino acid derivatives of the formula (V) are derived from optically active amino acids such as alanine, aminobutyric acid, valine, norvaline, leucine, isoleucine, ter-leucine, phenylglycine, phenylalanine, naphthylalanine, cyclohexyl-glycine, cyclohexylalanine, tyrosine, tryptophan, threonine, serine, aspartic acid, glutamic acid, ornithine, lysine or proline.

Very particularly preferred N-(meth)acryloylamino acid derivatives of the formula (I) are: N-(meth)acryloylalanine menthyl ester, N-(meth) acryloylalanine bornyl ester, N-(meth)acryloylalanine fenchyl ester, N-(meth)acryloylphenyl alanine methyl ester, N-methacryloyl-phenylglycine tert-butyl ester, N-methacryloylleucine tert-butyl ester, N-methacryloyl-phenylalanine tert-butyl ester, N-(meth)acryloyl-valine trans-4-tert-butylcyclohexyl ester, N-methacryloyl-N'-tert-butoxycarbonyl-lysine tert-butyl ester, N-methacryloyl-isoleucine tert-butyl ester, N-methacryloyl-valine tert-butyl ester, N-methacryloyl-cyclohexylalanine tert-butyl ester, N-(meth)-acryloyl-alanine 2-decahydronaphthyl ester, N-methacryloylalanine methylamide, N-methacryloyl-phenyl-alanine methylamide and N-methacryloylphenyl-alanine 1-phenylethylamide.

The optically active poly(meth)acrylamides containing the structural units of the formula (IV) are preferably present in the form of cross-linked insoluble but swellable polymers or in a form preferably bound to inorganic support materials.

The cross-linked polymers are furthermore preferably present in the form of finely divided beads having a particle diameter of 5 to 200 µm. They can be prepared in a manner known per se by suspension polymerization of the optically active (meth)acrylamide monomers of the formula (VI) with 0.5 to 50 mol %, preferably 1 to 20 mol %, particularly preferably 3 to 15 mol %, (based on the total amount (moles) of the monomers employed) of a suitable cross-linker.

Preferred network polymers are those which are derived from optically active diamines, dicarboxylic acids, diols or hydroxycarboxylic acids. Particularly preferred network polymers are those which are derived from tartaric acid derivatives which are disclosed in EP-A 671 975.

Preferred crown ethers are those of the general formula (VI)

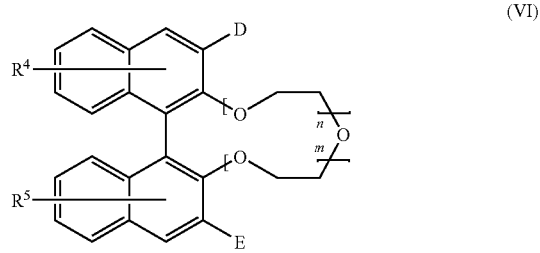

(VI)

in each case in the R,R or S,S form, having an optical purity of at least 95% ee, preferably at least 98% ee and particularly preferably at least 99% ee and in which D and E independently of one another, but preferably identically, represent hydrogen, $C_1$-$C_6$-alkyl, $C_6$-$C_{10}$-aryl or $C_7$-$C_{11}$-arylalkyl and $R^4$ and $R^5$ in each case independently of one another, but preferably identically, represent radicals which are selected from the group consisting of $C_1$-$C_{30}$-alkyl or $C_6$-$C_{10}$-aryl, where the number of radicals $R^4$ and $R^5$ on the naphthyl unit is in each case zero, one, two or three, but preferably in each case identically zero or one, where in each case substitution in the 6,6'-position is preferred and the sum of n+m is 3 to 10, preferably 4 to 8 and particularly preferably 5 or 6.

Chiral crown ethers of the formula (VI) in which D and E in each case identically represent phenyl, n+m=5 and the number of the radicals $R^4$ and $R^5$ is zero are particularly preferred.

As stationary chiral phases which contain chiral crown ethers, those are preferred which have crown ethers of the formula (VI) including the preferred ranges mentioned and are applied to silica gel. Such chiral phases are commercially available, for example, under the name Crownpak CR (+,−)® from Daicel.

Preferred derivatives of polysaccharides are those which are derived from natural or synthetic glucans, mannans, galactans, fructans, xylans or chitosans.

Preferably, derivatives of those polysaccharides are employed, which are derived from polysaccharides which have a regular mode of bonding in the chain. These are, for example, β-1,3-glucans such as in particular curdlan and schizophyllan, β-1,4-glucans such as in particular cellulose, β-1,6-glucans such as in particular pustulan, β-1,2-glucans such as in particular crown gall polysaccharides, α-1,3-glucans, α-1,4-glucans such as in particular amylose and amylopectin or starches, α-1,6-glucans such as in particular dextrans and cyclodextrans, a α-1,6-mannans, β-1,4-mannans, β-1,4-galactans, β-1,2-fructans such as in particular inulin, β-2,6-fructans such as in particular levan, β-1,3-xylans, β-1,4-xylans, β-1,4-chitosans, α-1,4-N-acetylchitosans such as in particular chitin. Particularly preferably, derivatives of those polysaccharides are employed which are derived from cellulose, chitin and amylose.

The average degree of polymerization of the polysaccharide (number average) can, for example, be and preferably is 5 to 500 monosaccharide units but in principle is not restricted upwardly.

The term "derivative of polysaccharides" is to be understood as meaning polysaccharides in which the hydrogen atoms of the hydroxy groups or in each case one hydrogen atom of the amino groups, but preferably the hydrogen atoms of the hydroxy groups, are substituted at least partially by radicals containing up to 30 carbon atoms. Preferably, at least 30%, particularly preferably at least 50% and very particularly preferably at least 80% of the hydrogen atoms of hydroxy groups or in each case of a hydrogen atom of amino groups are substituted. Preferred radicals having up to 30 carbon atoms are those of the formula (VIIa), $R^6$—                       (VIIa), in which $R^6$ represents $C_4$-$C_{14}$-aryl, or those of the formula (VIIb)

$R^7$-A-CO—                  (VIIb), in which $R^7$ represents $C_4$-$C_{14}$-aryl and at the same time A is absent or represents $C_1$-$C_4$-alkanediyl or $C_2$-$C_4$-alkenediyl or $R^7$ represents $C_1$-$C_4$-alkyl and at the same time A is absent, or those of the formula (VIIc)

$R^8$—B—NHCO—            (VIIc), in which $R^8$ represents $C_4$-$C_{14}$-aryl and B is absent or represents $C_1$-$C_4$-alkanediyl.

$C_4$-$C_{14}$-Aryl here represents, for example and preferably, carbocyclic aromatic radicals or heteroaromatic radicals, which contain no, one or two heteroatoms per cycle, in the entire heteroaromatic radical at least, however, one heteroatom, which are selected from the group consisting of nitrogen, sulphur and oxygen. Furthermore, the carbocyclic aromatic radicals or heteroaromatic radicals can be substituted with one, two, three, four or five substituents per cycle, which in each case independently of one another are selected for example and preferably from the group consisting of $C_1$-$C_4$-alkyl, nitro, cyano, O—($C_1$-$C_4$-alkyl), fluorine, chlorine, bromine, tri($C_1$-$C_4$-alkyl)silyl.

$C_1$-$C_4$-Alkyl here in each case independently represents a straight-chain, branched or unbranched $C_1$-$C_4$-alkyl radical such as, for example, methyl, ethyl, n-propyl, iso-propyl, n-butyl, sec-butyl and tert-butyl.

$C_1$-$C_4$-Alkanediyl here in each case independently represents a straight-chain, branched or unbranched $C_1$-$C_4$-alkanediyl radical such as, for example, methylene, (S)-1,1-ethylene, (R)-1,1-ethylene, 1,2-propanediyl and 1,3-propanediyl.

$C_2$-$C_4$-Alkenediyl here in each case independently represents a straight-chain, branched or unbranched $C_2$-$C_4$-alkenediyl radical such as, for example, ethenyl, 1,2-propenyl and 1,3-propenyl.

In formula (VIIa), $R^6$ preferably represents phenyl, which is substituted with no, one or two radicals, which in each case independently are selected from the group consisting of methyl, nitro, chlorine, bromine, tri($C_1$-$C_4$-alkyl)silyl.

In formula (VIIb), $R^7$ and A together preferably represent methyl, 2-phenylethenyl, phenyl or p-tolyl.

In formula (VIIc), $R^8$ and B together preferably represent (S) or (R)-phenylethyl, phenyl, 3,5-dimethylphenyl, p-tolyl and p-chlorophenyl, where 3,5-dimethylphenyl is even further preferred.

Stationary chiral phases in the context of the invention are preferably those which have chiral crown ethers of the formula (VI) including the preferred ranges mentioned and are applied to silica gel. Such chiral phases are commercially available, for example, under the name Crownpak CR (+,−)® from Daicel.

Furthermore, as stationary chiral phases in the context of the invention those are preferred which have derivatives of polysaccharides including the preferred ranges mentioned and are applied to silica gel. Such chiral phases are commercially available, for example, under the name Chiralpak® (AD, AS)™ or Chiralcel® (OD, OJ, OA, OB, OC, OF, OG, OK)™ from Daicel.

Particularly preferably, stationary chiral phases used in the context of the invention are those are which contain amylose tris(3,5-dimethylphenyl-phenylcarbamate), amylose tris-[(S)-α-methylbenzylcarbamate], cellulose tris(3,5-dimethylphenylcarbamate), cellulose tris(4-methylbenzoate) or cellulose tris(4-chlorphenylcarbamate) and are applied to silica gel (e.g., obtainable under the name Chiralpak® (AD, AS)™ or Chiralcel (OD, OJ, OF)™ from Daicel).

Very particularly preferred stationary chiral phases in the context of the invention are those which contain amylose tris(3,5-dimethylphenyl-carbamate) or cellulose tris(3,5-dimethylphenylcarbamate) and are applied to silica gel (e.g. obtainable under the name Chiralpak® (AD)™ or Chiralcel® (OD)™ from Daicel), where as stationary chiral phases those are even further preferred which contain amylose tris(3,5-dimethylphenylcarbamate) and are applied to silica gel [Chiralpak® (AD)™].

The starting mixture employed for the separation of enantiomers, which contains the enantiomers of cis-8-benzyl-7,9-dioxo-2,8-diazabicyclo-[4.3.0]nonane, is supplied to the circulating stream of liquid dissolved in a solvent as a "feedstream".

The proportion of the starting mixture in the feedstream can be, for example, 1 to 35 mass %, preferably 5 to 30 mass % and particularly preferably 15 to 30 mass %.

Suitable solvents are organic solvents. These are, for example and preferably, aliphatic hydrocarbons having 6 to 12 carbon atoms such as preferably methyl-cyclohexane, cyclohexane, n-hexane and n-heptane, ethers such as preferably tetrahydrofuran, aliphatic alcohols having 1 to 6 carbon atoms such as preferably methanol, ethanol and isopropanol, nitrites such as preferably acetonitrile, benzonitrile and benzyl nitriles or mixtures of such solvents.

n-Hexane, n-heptane, isopropanol and acetonitrile or mixtures thereof are particularly preferred, acetonitrile being even further preferred.

An eluting agent is furthermore supplied to the optionally circulating stream of liquid. The eluting agent is more advantageously an organic solvent, the abovementioned details including the preferred ranges applying in the same way. Particularly preferably, the same solvents are employed for the feedstream and the eluting agent.

If mixtures of solvents are employed, it is furthermore possible to change the composition during the addition of the eluting agent, which can take place, for example, at intervals or continuously in the form of a gradient.

In the context of the invention, it is preferred, however, to work at constant composition of the solvent. Even further preferred is the use of only one solvent.

Advantageously, organic solvents are used which have a water content of 3 mass % or less, preferably 0.3 mass % or less and particularly preferably 0.03 mass % or less.

The pressure during the addition of the feedstream and of the eluting agent can be, for example, 0.5 bar to 100 bar, 1 bar to 60 bar being preferred.

The temperature during the enantiomeric enrichment can be, for example, 0 to 80° C., preferably 10 to 40° C., particularly preferably 18 to 32° C. and very particularly preferably 20 to 28° C.

The raffinate and the extract can then be removed from the SMB unit, these fractions in each case containing an enriched enantiomer of cis-8-benzyl-7,9-dioxo-2,8-diazabicyclo [4.3.0]nonane, it being possible for the enriched enantiomers to be obtained by removal of the solvent, for example by evaporation.

In the manner according to the invention, the enantiomers of cis-8-benzyl-7,9-dioxo-2,8-diazabicyclo[4.3.0]nonane, in particular (1S,6R)-8-benzyl-7,9-dioxo-2,8-diazabicyclo [4.3.0]nonane, can be obtained, for example, with optical purities of 70% ee or more, preferably 85% ee or more, particularly preferably 90% ee or more and very particularly preferably 95% ee or more.

In the manner according to the invention, the enantiomer of the raffinate, preferably (1S,6R)-8-benzyl-7,9-dioxo-2,8-diazabicyclo[4.3.0]nonane, can be obtained, for example, with absolute purities of 90% or more, preferably 95% or more and particularly preferably 98% or more.

Furthermore, in the manner according to the invention, the enantiomer of the extract, preferably (1R,6S)-8-benzyl-7,9-dioxo-2,8-diazabicyclo-[4.3.0]nonane, can be obtained, for example, with absolute purities of 85% or more, preferably 90% or more and particularly preferably 95% or more.

The yields, based on the maximally obtainable amount of the enantiomers of cis-8-benzyl-7,9-dioxo-2,8-diazabicyclo [4.3.0]nonane, in particular (1S,6R)-8-benzyl-7,9-dioxo-2,8-diazabicyclo[4.3.0]nonane, can be 60% or more, preferably 80% or more and particularly preferably 95% or more.

It is a particular characteristic of the process according to the invention that the enantiomers of cis-8-benzyl-7,9-dioxo- 2,8-diazabicyclo-[4.3.0]nonane, in particular (1S,6R)-8-benzyl-7,9-dioxo-2,8-diazabicyclo-[4.3.0]nonane, can be obtained in optical purities of 95% ee or more with yields based on the maximally obtainable amount of the enantiomer of over 95%.

Furthermore, the enantiomers of cis-8-benzyl-7,9-dioxo-2,8-diazabicyclo[4.3.0]nonane, in particular (1S,6R)-8-benzyl-7,9-dioxo-2,8-diazabicyclo[4.3.0]nonane, can be obtained in optical purities of 90% ee or more with a productivity of over 0.2 kg, preferably over 0.8 kg and particularly preferably over 3.0 kg, per kg of chiral stationary phase per day [kg/(kg$_{CSP}$·d)].

If for a subsequent step only one enantiomer is of interest, it is advantageous to racemize the enriched undesired enantiomer and to add it again to the continuous countercurrent chromatography.

In a preferred embodiment, (1S,6R)-8-benzyl-7,9-dioxo-2,8-diazabicyclo-[4.3.0]nonane is obtained from the raffinate and the enantiomer (1R,6S)-8-benzyl-7,9-dioxo-2,8-diazabicyclo[4.3.0]nonane is racemized and added again to the continuous countercurrent chromatography.

The racemization is known in principle from EP-A 1067 129 and carried out by addition of base.

In this case, for the racemization, for example, pure (1R,6S)-8-benzyl-7,9-dioxo-2,8-diazabicyclo[4.3.0]nonane or mixtures can be employed which contain, for example, over 70% by weight, preferably over 85% by weight, of (1R,6S)-8-benzyl-7,9-dioxo-2,8-diazabicyclo[4.3.0]nonane. Making up to 100%, these mixtures can contain, for example, (1S,6R)-8-benzyl-7,9-dioxo-2,8-diazabicyclo[4.3.0]nonane.

Furthermore, it is possible and preferred to employ the enantiomer to be racemized, preferably (1R,6S)-8-benzyl-7,9-dioxo-2,8-diazabicyclo-[4.3.0]nonane, directly in the form of the raffinate or extract solution from the enantiomeric enrichment. Customarily, (1R,6S)-8-benzyl-7,9-dioxo-2,8-diazabicyclo[4.3.0]nonane is obtained in the form of the extract solution.

Optionally, the raffinate or extract solution can be concentrated by evaporation of solvent.

Suitable bases for the racemization are, for example, alkoxides of the formula (VIII), $$MOR^9 \quad (VIII),$$

in which

M represents lithium, sodium or potassium, preferably sodium or potassium and $R^9$ represents a straight-chain or branched $C_1$-$C_6$-alkyl, preferably methyl or tert-butyl.

Preferred individual compounds of the formula (VIII) are sodium methoxide, sodium tert-butoxide and potassium tert-butoxide. Potassium tert-butoxide is particularly preferred.

Preferably, the base is employed in an amount of from 1 to 20 mol based on the amount of cis-8-benzyl-7,9-dioxo-2,8-diazabicyclo[4.3.0]nonane to be racemized.

The alkoxides can be added in solid form or dissolved in a solvent. Suitable solvents are, for example, alcohols and aprotic solvents, for example the alcohol which corresponds to the alkoxide employed in each case, and straight-chain, branched and cyclic ethers as well as aromatic hydrocarbons. Individual examples of aprotic solvents are: methyl tert-butyl ether, tetrahydrofuran, dioxane, toluene and xylene. Preferred alkoxide solutions are: potassium tert-butoxide in tert-butanol and in tetrahydrofuran and sodium methoxide in methanol.

In a preferred embodiment, the alkoxide is added to the solvent which serves as the eluting agent in the chromatographic separation.

The racemization can be carried out, for example, at temperatures between −10 and 40° C.

The racemization according to the invention is in general complete after, at the latest, 5 hours. Under suitable reaction conditions (e.g. appropriate choice of the base, of the solvent and of the temperature), the reaction time necessary can be significantly shorter and can be, for example, 15 minutes or even less.

The reaction mixture present after the racemization can be worked up such that the base employed is firstly neutralized, e.g. by addition of an organic acid, e.g. of a $C_1$-$C_6$-carboxylic acid, of a mineral acid, e.g. sulphuric acid or phosphoric acid, of carbonic acid or of an acidic ion exchanger. The amount of the acid or of the acidic ion exchanger can be, for example, 0.9 to 1.1 equivalents per equivalent of base employed. Preferably, this amount is 0.97 to 1.03 equivalents per equivalent of base employed, in particular the acid or the acidic ion exchanger is employed in equivalent amount, based on the base employed. Afterwards, the solvent can be removed, e.g. by distillation, optionally under reduced pressure. A racemization mixture remains which contains the enantiomers of cis-8-benzyl-7,9-dioxo-2,8-diazabicyclo-[4.3.0]nonanes in a molar ratio of 1:1 to 1.5:1, preferably 1:1 to 1.1:1, it of course being possible for only that enantiomer to be present in an excess which was employed in enriched form for the racemization.

If before, during or after implementation, solvents are removed which were employed as eluting agents, these can be employed again for the process according to the invention.

The racemization mixture can then either be stored or added again to the enantiomeric enrichment. This process course, enantiomeric enrichment, racemization, enantiomeric enrichment, can be repeated as often as desired, optionally with continuous readdition of starting mixture, so that, in the manner according to the invention, finally, for example, the racemic mixture of cis-8-benzyl-7,9-dioxo-2,8-diazabicyclo[4.3.0]nonanes obtained in the nuclear hydrogenation of pyridine-2,3-dicarboxylic acid N-benzylimide can be converted completely into an enriched enantiomer, preferably (1S,6R)-8-benzyl-7,9-dioxo-2,8-diazabicyclo[4.3.0]nonane with high absolute and optical purity.

The enriched enantiomers (1S,6R)-8-benzyl-7,9-dioxo-2,8-diazabicyclo-[4.3.0]nonane and (1R,6S)-8-benzyl-7,9-dioxo-2,8-diazabicyclo-[4.3.0]nonane obtainable in the manner according to the invention are suitable, in particular, in a process for the preparation of antibacterial agents and food additives.

Furthermore, the enriched enantiomer (1S,6R)-8-benzyl-7,9-dioxo-2,8-diazabicyclo-[4.3.0]nonane obtainable in the manner according to the invention is suitable for the preparation of (S,S)-2,8-diazabicyclo[4.3.0]nonane and moxifloxacin (INN, 1-cyclopropyl-7-([S,S]-2,8-diazabicyclo[4.3.0]non-8-yl)-6-fluoro-1,4-dihydro-8-methoxy-4-oxo-3-quinolonecarboxylic acid, the enriched enantiomer (1R,6S)-8-benzyl-7,9-dioxo-2,8-diazabicyclo[4.3.0]nonane for the preparation of (R,R)-2,8-diazabicyclo[4.3.0]nonane.

The process according to the invention is distinguished in that, in a continuous process, (1S,6R)-8-benzyl-7,9-dioxo-2,8-diazabicyclo-[4.3.0]nonane and (1R,6S)-8-benzyl-7,9-dioxo-2,8-diazabicyclo-[4.3.0]nonane can be obtained in high purity, optical purity and high yield with unexpected productivity. By means of a downstream racemization and recycling to the separation process, it is furthermore possible in a particularly advantageous manner to obtain a single target enantiomer, in particular (1S,6R)-8-benzyl-7,9-dioxo-2,8-diazabicyclo[4.3.0]nonane, in a very highly efficient manner.

EXAMPLES

Example 1

A continuously operating countercurrent chromatography unit from NovaSep, France, was employed (type: LICOSEP 8-200). Characteristic components of the unit are 8 axial flow columns (diameter in each case 200 mm) having a device for the dynamic axial compression of the stationary phase.

All external feeds and drains are in each case fed to specific sites or drained by means of appropriate connections, which correspond with the recirculating concentration profile. The following quantitative flows are established:
Zone I: 500 l/h
Zone II: 260.0 l/h
Zone III: 274.5 l/h
Zone IV: 200.0 l/h
Eluting agent: 300 l/h (acetonitrile, water content: <300 ppm)
Feedstream: 14.5 l/h
with 199.4 mg of rac-DOPP/ml (solvent: acetonitrile, water content <300 ppm)
Raffinate: 74.5 l/h of (1S,6R)-8-benzyl-7,9-dioxo-2,8-diazabicyclo[4.3.0]nonane in acetonitrile
Extract: 240.0 l/h h of (1R,6S)-8-benzyl-7,9-dioxo-2,8-diazabicyclo[4.3.0]nonane in acetonitrile
Cycle time: 0.72 min
Temperature: 25° C.
Chiral stationary phase: Chiralpak®AD™, 20 μm The compositions of the feedstream and of the extract are specified in Table 1 below. The yield is quantitative.

TABLE 1

| Extract | | Raffinate | | Productivity |
|---|---|---|---|---|
| % ee | %* | % ee | %* | $kg_{rac}/kg_{CSP}/d$ |
| 95.6 | 96.4 | 98.4 | 98.8 | 5.42 |

*Product stream without solvent or eluting agent

Example 2

A continuously operating countercurrent chromatography unit from NovaSep, France, was employed (type: LICOSEP 8-200). Characteristic components of the unit are 7 axial flow columns (diameter in each case 200 mm) having a device for the dynamic axial compression of the stationary phase, which used the configuration 2:2:2:1 (Zone1:Zone2:Zone3:Zone4).

All external feeds and drains are fed to specific sites or drained by means of appropriate connections, which correspond with the recirculating concentration profile. The following quantitative streams were established:
Zone I: 500 l/h
Zone II: 286.5 l/h
Zone III: 297.0 l/h
Zone IV: 200.0 l/h
Eluting agent: 300 l/h (acetonitrile, water content: <300 ppm)
Feedstream: 10.5 l/h
with 202.7 mg of rac-DOPP/ml (solvent: acetonitrile, water content <300 ppm)
Raffinate: 97 l/h of (1S,6R)-8-benzyl-7,9-dioxo-2,8-diazabicyclo[4.3.0]nonane in acetonitrile
Extract: 213.5 l/h of (1R,6S)-8-benzyl-7,9-dioxo-2,8-diazabicyclo[4.3.0]nonane in acetonitrile
Cycle time: 0.69 min
Temperature: 27° C.
Chiral stationary phase: Chiralpak®AD™, 20 μm The compositions of the feedstream and of the extract are specified in Table 2 below. The yield is quantitative.

TABLE 2

| Extract | | Raffinate | | Productivity |
|---|---|---|---|---|
| % ee | %* | % ee | %* | $kg_{rac}/kg_{CSP}/d$ |
| >99.9 | 96.3 | >99.9 | 98.9 | 4.56 |

*Product stream without solvent or eluting agent

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the enantiomeric enrichment of cis-8-benzyl-7,9-dioxo-2,8-diazabicyclo[4.3.0]nonane, comprising carrying out the enantiomeric enrichment by continuous countercurrent chromatography with the aid of an SMB unit.

2. Process according to claim 1, characterized in that a stream of liquid moving in one direction and optionally circulating is produced in the SMB unit by means of two or more segments connected to one another, each segment having at least one column filled with a chiral stationary phase and being provided in the flow direction at least with a liquid inlet and a liquid outlet and each segment having at least one inlet, via which a feedstream or an eluting agent can be fed to the optionally circulating stream of liquid, furthermore having at least one outlet, via which solutions of the more weakly adsorbing compound (raffinate) or solutions of the more strongly adsorbing compound (extract) can be removed from the optionally circulating stream of liquid.

3. Process according to claim 1, characterized in that the SMB unit has a column number of 4 to 24.

4. Process according to claim 1, characterized in that the SMB unit contains columns which are designed as cylindrical axial flow columns and have a device for dynamic compression.

5. Process according to claim 1, characterized in that the SMB unit contains columns which have a column diameter of 5 to 1500 mm.

6. Process according to claim 1, characterized in that the SMB unit contains columns which have a column length of 15 mm to 300 mm.

7. Process according to claim 2, characterized in that a closed circulation with a circulating stream of liquid is produced in the SMB unit.

8. Process according to claim 1, characterized in that, for the enantiomeric enrichment, a starting mixture is employed which contains the enantiomers of cis-8-benzyl-7,9-dioxo-2,8-diazabicyclo[4.3.0]nonane in a molar ratio of 0.25:1 to 4:1.

9. Process according to claim 1, characterized in that the cis-8-benzyl-7,9-dioxo-2,8-diazabicyclo[4.3.0]nonane is obtained by nuclear hydrogenation of pyridine-2,3-dicarboxylic acid-N-benzylimide.

10. Process according to claim 9, characterized in that the enantiomeric enrichment is carried out in the presence of trans-8-benzyl-7,9-dioxo-2,8-diazabicyclo[4.3.0]nonane or its enantiomers and/or other organic by-products originating from the nuclear hydrogenation of pyridine-2,3-di-carboxylic acid N-benzylimide.

11. Process according to claim 1, characterized in that, for the enantiomeric enrichment, columns are employed which, as a chiral stationary phase, contain polysaccharides, chiral polyacrylates, or chiral crown ethers, which are optionally applied to a support material.

12. Process according to claim 1, characterized in that, as chiral stationary phases, those are used which contain amylose tris(3,5-dimethyl phenylcarbamate), amylose tris[(S)-α-methylbenzyl-carbamate], cellulose tris(3,5-dimethylphenylcarbamate), cellulose tris(4-methylbenzoate) or cellulose tris(4-chlorphenylcarbamate) and are applied to silica gel.

13. Process according to claim 11, characterized in that, as a chiral stationary phase, those are used which contain amylose tris(3,5-dimethylphenylcarbamate) or cellulose tris(3,5-dimethylphenylcarbamate) and are applied to silica gel.

14. Process according to claim 1, characterized in that the solvents employed are aliphatic hydrocarbons having 6 to 12 carbon atoms, ethers, aliphatic alcohols having 1 to 6 carbon atoms, nitriles or mixtures of such solvents.

15. Process according to claim 1, characterized in that the solvent employed is acetonitrile.

16. Process according to claim 1, characterized in that the solvents used are those which have a water content of 3 mass % or less.

17. Process according to claim 1, characterized in that the pressure during the feed of the feedstream and of the eluting agent is 0.5 bar to 100 bar.

18. Process according to claim 1, characterized in that the temperature during the enantiomeric enrichment is 0 to 80° C.

19. Process according to claim 1, characterized in that the enantiomers of cis-8-benzyl-7,9-dioxo-2,8-diazabicyclo[4.3.0]nonane having optical purities of 70% ee or more are obtained.

20. Process according to claim 1, characterized in that the enantiomers of cis-8-benzyl-7,9-dioxo-2,8-diazabicyclo[4.3.0]nonanes are obtained with optical purities of 90% ee or more having a productivity of over 0.2 kg per kg of chiral stationary phase per day.

21. Process according to claim 1, characterized in that the enriched, undesired enantiomer is racemized.

22. Process according to claim 21, characterized in that the enriched undesired enantiomer is racemized and fed again to the continuous countercurrent chromatography.

23. Process according to claim 21, characterized in that (1S,6R)-8-benzyl-7,9-dioxo-2,8-diazabicyclo[4.3.0]nonane is obtained and the enantiomer (1R,6S)-8-benzyl-7,9-dioxo-2,8-diazabicyclo[4.3.0]nonane is racemized and fed again to the continuous countercurrent chromatography.

* * * * *